US00PP22754P2

(12) United States Plant Patent
Trees

(10) Patent No.: US PP22,754 P2
(45) Date of Patent: May 22, 2012

(54) ***SALVIA* PLANT NAMED 'BURGUNDY CANDLES'**

(50) Latin Name: *Salvia nemorosa*
Varietal Denomination: Burgundy Candles

(75) Inventor: Scott C. Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 13/136,131

(22) Filed: Jul. 25, 2011

(51) Int. Cl.
*A01H 5/00* (2006.01)

(52) U.S. Cl. ..... Plt./475

(58) Field of Classification Search ..... Plt./475
See application file for complete search history.

*Primary Examiner* — Howard Locker
(74) *Attorney, Agent, or Firm* — Audrey Charles

(57) ABSTRACT

A new and distinct cultivar of *Salvia* plant named 'Burgundy Candles', characterized by its deep violet-blue colored flowers, green and burgundy colored bracts, dark green-colored foliage, and vigorous, upright growth habit, is disclosed.

2 Drawing Sheets

Latin name of genus and species of plant claimed: *Salvia nemorosa.*

Variety denomination: 'Burgundy Candles'.

BACKGROUND OF THE INVENTION

The present invention relates to a new and distinct cultivar of *Salvia* plant botanically known as *Salvia nemorosa* and hereinafter referred to by the cultivar name 'Burgundy Candles'.

The new cultivar originated in a controlled breeding program in Arroyo Grande, Calif. during September 2006. The objective of the breeding program was the development of *Salvia* cultivars having large flowers with distinctive coloration.

The new *Salvia* cultivar is the result of open-pollination. The female (seed) parent of the new cultivar is *Salvia nemorosa* 'Caradonna', not patented, characterized by its deep purple-colored flowers, medium green-colored foliage, dark purple-colored stems, and vigorous, upright growth habit. The male (pollen) parent of the new cultivar is unknown. The new cultivar was discovered and selected as a single flowering plant within the progeny of the above stated open-pollination during August 2007 in a controlled environment in Arroyo Grande, Calif.

Asexual reproduction of the new cultivar by terminal stem cuttings since August 2007 in Arroyo Grande, Calif. and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Burgundy Candles' as a new and distinct cultivar of *Salvia* plant:

1. Deep violet-blue colored flowers;
2. Green and burgundy colored bracts;
3. Dark green-colored foliage; and
4. Vigorous, upright growth habit.

Plants of the new cultivar differ from plants of the female parent primarily in bract and stem coloration.

Of the many commercially available *Salvia* cultivars, the most similar in comparison to the new cultivar is 'May Night', not patented. However, in side by side comparisons, plants of the new cultivar differ from plants of 'May Night' in at least the following characteristics:

1. Plants of the new cultivar have a flower color different from plants of 'May Night'; and
2. Plants of the new cultivar have a bract color different from plants of 'May Night'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Burgundy Candles'.

The plants were grown in 1-gallon pots for 16 weeks in a greenhouse in Elburn, Ill.

Plants were given one pinch at transplant.

DETAILED BOTANICAL DESCRIPTION

Figure 1:
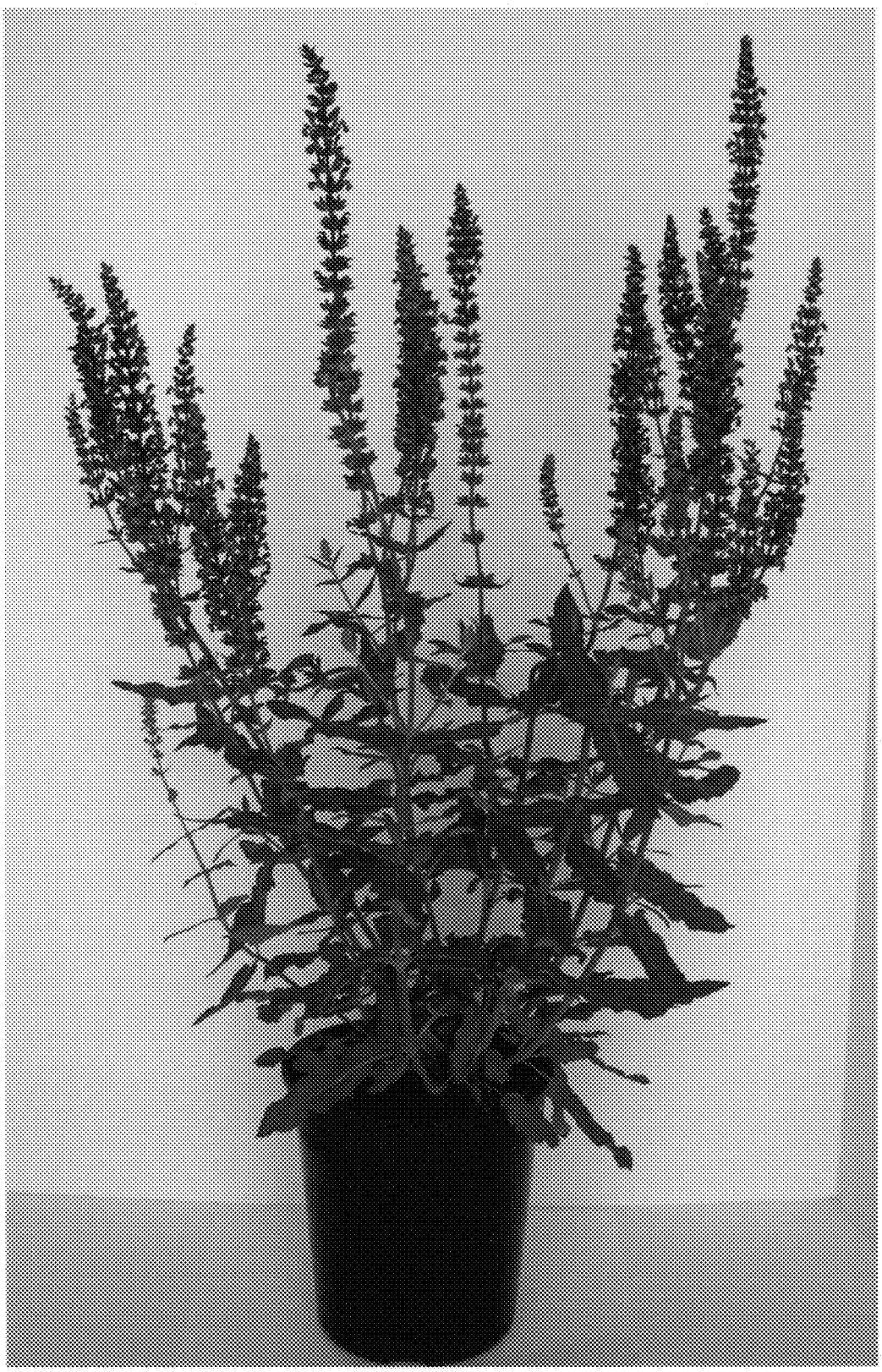
FIG. 1 illustrates a side view of the overall growth and flowering habit of 'Burgundy Candles'.
Figure 2:
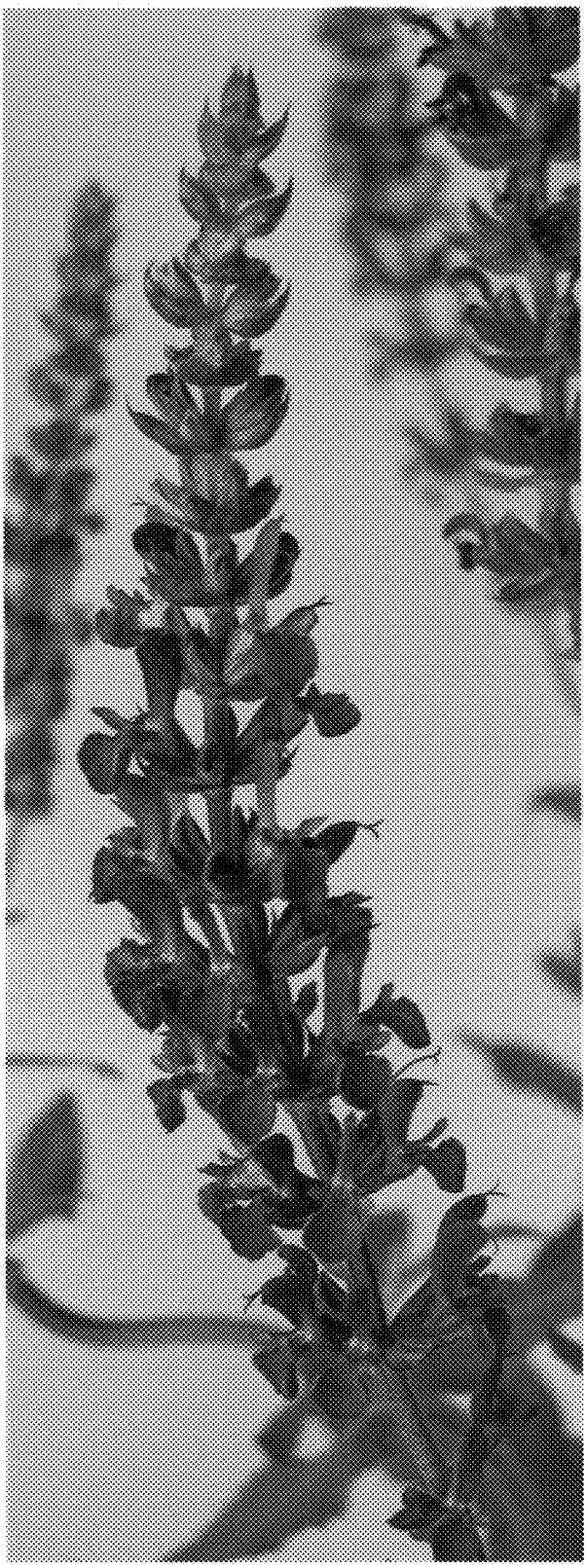
FIG. 2 illustrates a close-up view of an inflorescence of 'Burgundy Candles'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2011 under natural light conditions in West Chicago, Ill.

The following descriptions and measurements describe plants produced from cuttings from stock plants and grown in a glass-covered greenhouse under conditions comparable to those used in commercial practice. The plants were grown in Elburn, Ill. in 1-gallon pots for 16 weeks utilizing a soilless growth medium. Plants were given one pinch at transplant. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Salvia nemorosa* cultivar Burgundy Candles.

Parentage:

*Female parent*.—*Salvia nemorosa* 'Caradonna', not patented.

*Male parent*.—Unknown.

Propagation:

*Type cutting*.—Terminal stem.

*Time to initiate roots*.—Approximately 9 to 12 days.

*Time to produce a rooted cutting*.—Approximately 24 to 28 days.

*Root description*.—Fine, fibrous white to dark brown in color.

*Rooting habit*.—Freely branching.

Plant description:

*Commercial crop time*.—Approximately 12 to 16 weeks from a rooted cutting to finish in a 15 cm pot.

*Growth habit and general appearance*.—Vigorous, upright.

*Size*.—Height from soil level to top of plant plane: Approximately 62.5 cm. Width: Approximately 40.5 cm.

*Branching habit*.—Freely branching. Pinching enhances lateral branching. Quantity of branches per plant: Approximately 11.

*Branch*.—Shape: Square in cross section. Strength: Strong. Length to base of inflorescence: Approximately 34.0 cm. Diameter: Approximately 4.0 mm. Length of central internode: Approximately 6.7 cm. Texture: Densely pubescent with appressed, soft, short hairs. Color of young and mature stems: 138A to 138B with streaks of N187A.

Foliage description:

*General description*.—Quantity of leaves per branch: Approximately 10. Fragrance: Strong, sage-like. Form: Simple. Arrangement: Opposite.

*Leaves*.—Aspect: Perpendicular angle to stem. Shape: Ovate to elliptic. Margin: Crenate. Apex: Acute. Base: Obtuse to cordate. Venation pattern: Pinnate. Length of mature leaf: Approximately 8.0 cm. Width of mature leaf: Approximately 2.5 cm. Texture of upper and lower surfaces: Rugous, densely pubescent. Color of upper surface of young and mature foliage: N137A with venation of 145C. Color of lower surface of young and mature foliage: Lighter than N137D with venation of 145C.

*Petiole*.—Length: Approximately 8.0 mm. Diameter: Approximately 4.0 mm. Texture: Densely pubescent. Color: 145C.

Flowering description:

*Flowering habit*.—'Burgundy Candles' is freely flowering under outdoor growing conditions blooming from spring through autumn and with limited flowering under short winter days in a greenhouse environment.

*Lastingness of individual floret*.—Approximately 4 to 5 days.

Inflorescence description:

*General description*.—Type: Spikes in verticillaster arrangement, florets in clusters of three, not persistent. Quantity of inflorescences per plant: Approximately 26. Fragrance: Faint, sweet. Length or height of inflorescence: Approximately 14.0 cm. Width of inflorescence: Approximately 2.3 cm. Quantity of fully-open flowers per inflorescence: Approximately 45 with up to 84 at peak flowering.

*Peduncle*.—Shape: Square in cross section. Strength: Strong. Aspect: Erect. Length: Approximately 4.0 cm. Diameter: Approximately 3.0 mm. Texture: Densely pubescent with appressed, soft, short hairs. Color: 138A with streaks of N187A.

Flower description:

*Type*.—Single, zygomorphic.

*Bud*.—Rate of opening: Generally takes 2 to 3 days for bud to progress from first color to fully open flower.

*Bud just before opening*.—Shape: Ovoid. Length: Approximately 5.0 mm. Diameter: Approximately 2.0 mm. Texture: Densely pubescent. Color: calyx of 138B with venation of N187A; petals of N89C.

*Corolla*.—Shape: Bilabiate, lower lip having three lobes, based fused. Width: Approximately 5.0 mm. Length: Approximately 9.0 mm. Depth: Approximately 1.1 cm.

*Upper lip*.—Shape: Hooded with revolute edges. Margin: Entire. Apex: Emarginate. Length from throat: Approximately 6.0 mm. Width: Approximately 1.5 mm. Texture of inner surface: Glabrous. Texture of outer surface: Sparsely pubescent. Color of inner surface when first and fully open: N89C. Color of outer surface when first and fully open: N89A.

*Lower lip*.—Shape of central lobe: Orbicular, cupped. Shape of lateral lobes: Elliptic. Margin: Entire. Apex of central lobe: Rounded. Apex of lateral obes: Acute. Length from throat of central lobe: Approximately 4.0 mm. Width of central lobe: Approximately 5.0 mm. Length from throat of ateral lobes: Approximately 3.0 mm. Width of lateral lobes: Approximately 1.0 mm. Texture of upper surface: Glabrous. Texture of lower surface: Sparsely pubescent. Color of upper surface when first and fully open: N89A. Color of lower surface when first and fully open: N89C.

*Calyx*.—Shape: Tubular. Length: Approximately 6.0 mm. Diameter: Approximately 4.0 mm.

*Sepals*.—Quantity per flower: 5, fused. Shape: Elliptic. Apex: Acute. Length: Approximately 6.0 mm. Width: Approximately 2.0 mm. Texture of inner surface: Glabrous. Texture of outer surface: Densely pubescent. Color of inner surface: 138B. Color of outer surface: 138B with venation and margins of N187A.

*Bracts*.—Quantity: One bract located at the base of floret cluster. Length: Approximately 6.0 mm. Width: Approximately 5.0 mm. Texture: Glabrous with densely pubescent margins. Color of upper and lower surfaces: 138A with an overlay of closest to N77B.

*Pedicel*.—Strength: Strong, flexible. Aspect: At an acute angle. Length: Approximately 1.0 mm. Diameter: Less than 1.0 mm. Texture: Densely pubescent. Color: N187A.

*Reproductive organs*.—Androecium: Stamen quantity: 2 per flower, dorsifixed, strongly curved. Filament length: Approximately 6.0 mm. Filament color: NN155C, opaque. Anther shape: Narrowly elliptic to oblong. Anther length: Approximately 2.0 mm. Anther color: 203D. Pollen amount: Moderate. Pollen color: 7A. Gynoecium: Pistil quantity: 1 per flower, strongly curved. Pistil length: Approximately 1.2 cm. Stigma shape: Cleft, two-parted. Stigma color: N89B. Style length: Approximately 1.0 cm. Style color: NN155C, opaque. Ovary length: Approximately 1.0 mm. Ovary color: 144C.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Burgundy Candles', substantially as herein shown and described.

* * * * *